(12) United States Patent
Versemann et al.

(10) Patent No.: US 6,660,025 B2
(45) Date of Patent: Dec. 9, 2003

(54) BODY ILLUMINATING DEVICE WITH ALTERNATING LONGITUDINALLY OFFSET TUBULAR LAMPS

(75) Inventors: Michael Wayne Versemann, Indianapolis, IN (US); Gary Weiler, Beech Grove, IN (US)

(73) Assignee: Spectrum Products, Inc., Indianapolis, IN (US)

( * ) Notice: Subject to any disclaimer, the term of this patent is extended or adjusted under 35 U.S.C. 154(b) by 111 days.

(21) Appl. No.: 09/960,443

(22) Filed: Sep. 21, 2001

(65) Prior Publication Data

US 2003/0060861 A1 Mar. 27, 2003

(51) Int. Cl.[7] .................................................. A61N 5/06
(52) U.S. Cl. ........................ 607/94; 607/88; 607/89; 607/93; 607/91; 250/504 R
(58) Field of Search ........................... 607/88, 90, 91, 607/93, 94; 250/504 R

(56) References Cited

U.S. PATENT DOCUMENTS

| | | | |
|---|---|---|---|
| 4,623,796 A | 11/1986 | Kratz | 250/504 R |
| 4,683,888 A * | 8/1987 | Kramer et al. | 128/376 |
| 4,703,184 A | 10/1987 | Wolff | 250/504 R |
| 5,683,437 A | 11/1997 | Doty | 607/91 |
| 6,139,568 A | 10/2000 | Doty | 607/91 |
| 6,494,901 B1 * | 12/2002 | Doty | 607/91 |

OTHER PUBLICATIONS

ETS, Inc. Catalog; 1991; p. 9.
ETS, Inc. Catalog; 1992; p. 15, 19.
Sun Industries; National Journal of Indoor Tanning & Recreation; 1993; cover.
ETS, Inc. (Wolff Tanning Equipment) Catalog; 1998; cover, p. 13, 17, 19.

* cited by examiner

Primary Examiner—Linda C. M. Dvorak
Assistant Examiner—Ahmed Farah
(74) Attorney, Agent, or Firm—Woodard, Emhardt, Moriarty, McNett & Henry LLP

(57) ABSTRACT

A tanning bed has an array of closely spaced ultraviolet-emitting, fluorescent lamps in which each lamp is longitudinally offset from an adjacent lamp to allow space for grasping of one end to rotate the lamp for removal of the lamp from its sockets.

54 Claims, 4 Drawing Sheets

BODY ILLUMINATING DEVICE WITH ALTERNATING LONGITUDINALLY OFFSET TUBULAR LAMPS

FIELD OF THE INVENTION

This invention relates to a light emitting device for illuminating the body, including illuminating a portion thereof. Examples of such devices include a tanning bed, tanning canopy, tanning booth, or face tanner. In particular, the invention relates to an arrangement of lamps that increases the total number of tubular lamps in an array in a body illuminating device while preserving the ability to grasp the lamps during removal or installation.

BACKGROUND OF THE INVENTION

Arrangements of tubular ultraviolet fluorescent lamps have been used for, among other things, tanning beds, tanning booths, face tanners and tanning canopies. The present invention relates to an apparatus having an arrangement of fluorescent lamps, preferably tubular tanning lamps. Maximizing the total number of ultraviolet lamps while maintaining a constant distance from the body, yet preserving the ability to grasp the lamps for removal or installation is commercially desirable. To maximize the number of lamps in a bed, various arrangements of lamps have arisen. U.S. Pat. Nos. 6,139,568 to Doty; 5,683,437 to Doty; 4,703,184 to Wolff; and 4,623,796 to Kratz are cited as background references concerning various lamp arrangement schemes.

In one approach, the lamps in the same row are simply placed closer together. The drawback to this approach is that the minimum separation between the lamps is limited to allow for grasping of the lamps, thereby limiting the minimum lamp separation and thus maximum number of lamps in the bed. Another approach uses two rows of lamps having different distances from the person being illuminated or tanned. The lamps in each row are separated such that the lamps may be grasped for removal or installation with the lamps in the back row being placed behind the gaps between the lamps in the front row. This staggering of the lamps between the rows allows the radiation from the row further away from the tanning person to directly emit radiation onto the tanning person through the gaps between the lamps in the closest row. This configuration increases the total number of tanning lamps in a tanning bed while leaving sufficient space between individual lamps in each row to facilitate grasping the lamps. However, a drawback to this design is that the tanning bed must be bulkier to accommodate two rows of lamps, and the lamps in the more remote row are further away than desired.

A need exists for a lamp arrangement that allows the lamps in the same row to be closely spaced while still allowing grasping of the lamps for individual replacement. The present invention satisfies these needs and provides other important advantages.

SUMMARY OF THE INVENTION

The present invention allows lamps in a body illuminating device to be placed closely together while still allowing individual lamps to be grasped. Longitudinally displacing a lamp from the lamp next to it creates a space at the end of the lamp whereby the lamp may be grasped for installing or removing the lamp. Since this offset alleviates the need to grip the lamps near the center, the spacing between the lamps may be decreased to the point where adjacent lamps are almost, or actually, touching. When removing or installing lamps, one end of each lamp may be gripped and rotated to remove or install each lamp.

DESCRIPTION OF THE ILLUSTRATIVE EMBODIMENTS

Figure 1:
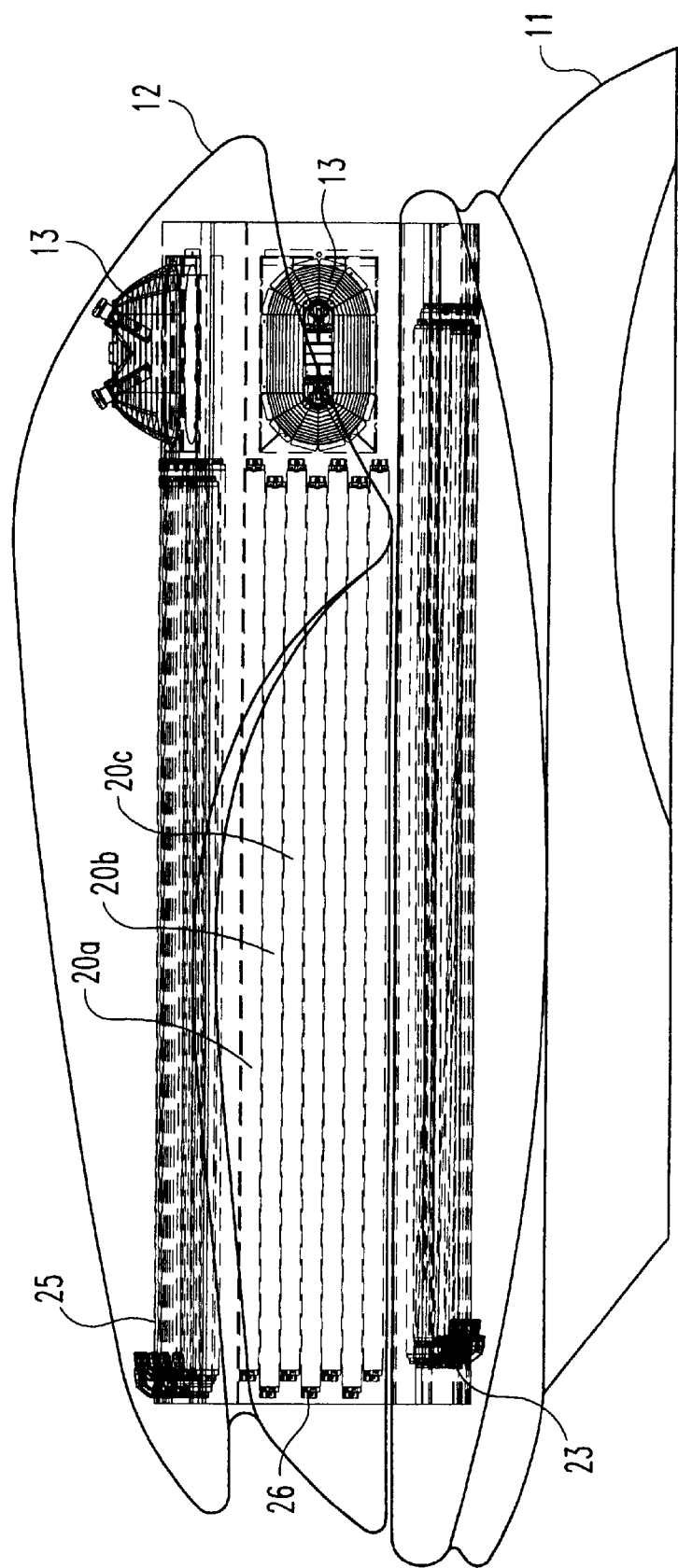
FIG. 1 is a side view of the invention being used in one embodiment of the tanning bed.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

FIG. 1 depicts a tanning bed having a lamp arrangement whereby each ultraviolet fluorescent lamp 20 is attached to a base support member 11 and each ultraviolet lamp 20 is staggered longitudinally from a lamp adjacent to it. The term longitudinal as used herein correlates to the orientation of the axis of the substantially parallel tanning lamps. The tanning person (not shown) lays inside bounded by the bottom array of lamps 23, the back-side array of lamps 24, (depicted in FIG. 4), the top array of lamps 25, and the front-side of lamps 26. The canopy 12 includes both the front-side array of lamps 26 and the top array of lamps 25. Specialized facial tanning units 13 are also placed in the tanning bed in the area around where the tanning person's head lies.

Figure 2:
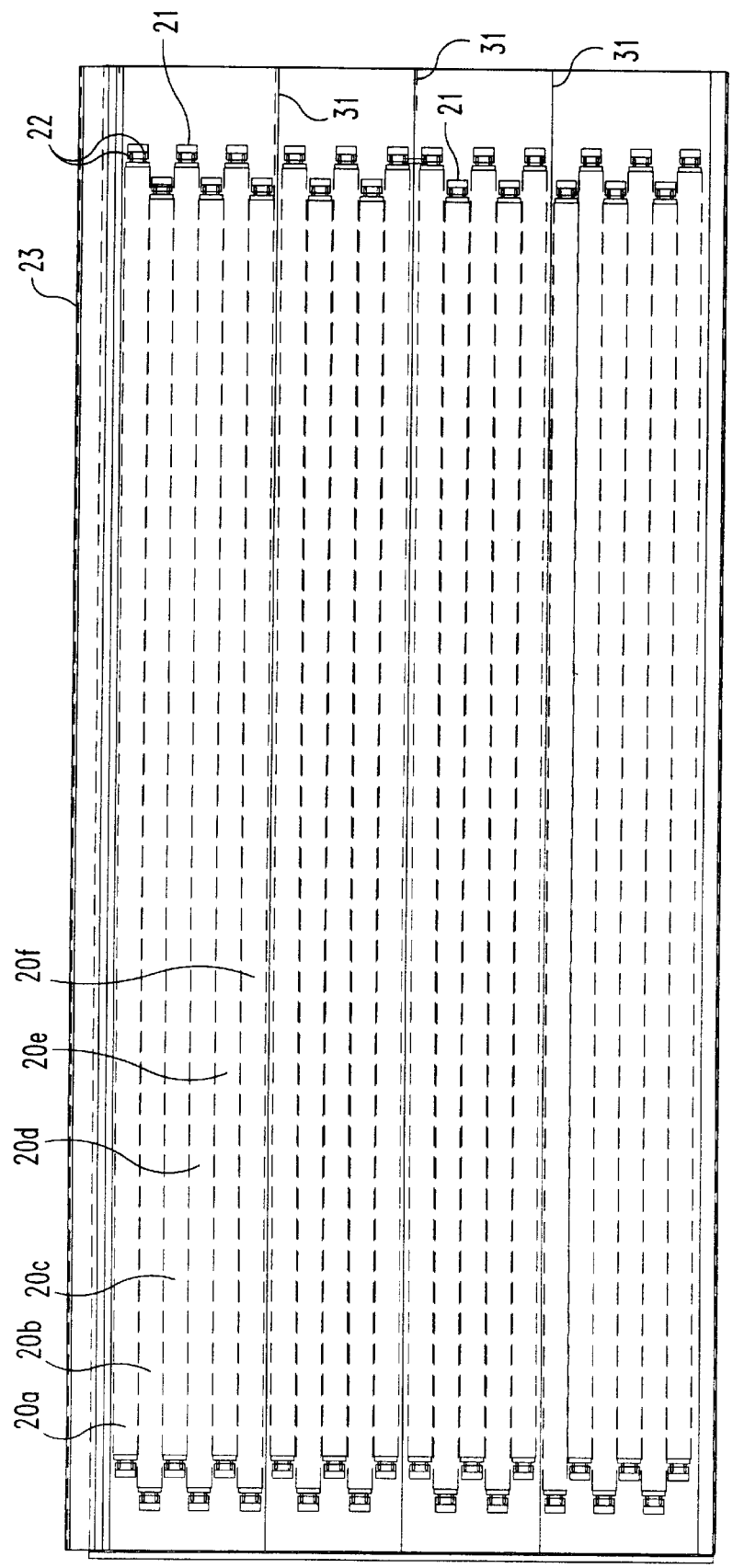
FIG. 2 is a top plan view of the lower lamp array showing one embodiment of FIG. 1 where every other row is offset.

FIG. 2 depicts the bottom array of lamps 23 in a first embodiment that contains the offset arrangement of lamps. Although depicted in the bottom array, the offset arrangement is used throughout the tanning bed. Each lamp 20 is of similar diameter and has two electrical connectors 22 at each end that insert into conductive electrical sockets 21 at each end, and may be of conventional design for fluorescent lamps. These electrical sockets 21 are connected to the base support member 11. Every other lamp 20 is staggered longitudinally from the lamp next to it by about one and one-quarter inches. Thus, lamp 20b is displaced longitudinally one and one-quarter inches from lamp 20a, and lamp 20c is offset one and one-quarter inches from lamp 20b while being roughly aligned with lamp 20a. This staggering pattern continues throughout the array. Thus, the respective ends of every other lamp are roughly aligned with each other. For example, lamps 20a, 20c, and 20e are roughly aligned and offset from lamps 20b, 20d, and 20f, which are roughly aligned with each other. Each array of lamps may be further subdivided into sections by supports 31 that maintain separation between the transparent protective acrylic 30 (depicted in FIG. 4) and the lamps 20 while pressure is being applied to the acrylic 30.

Figure 3:
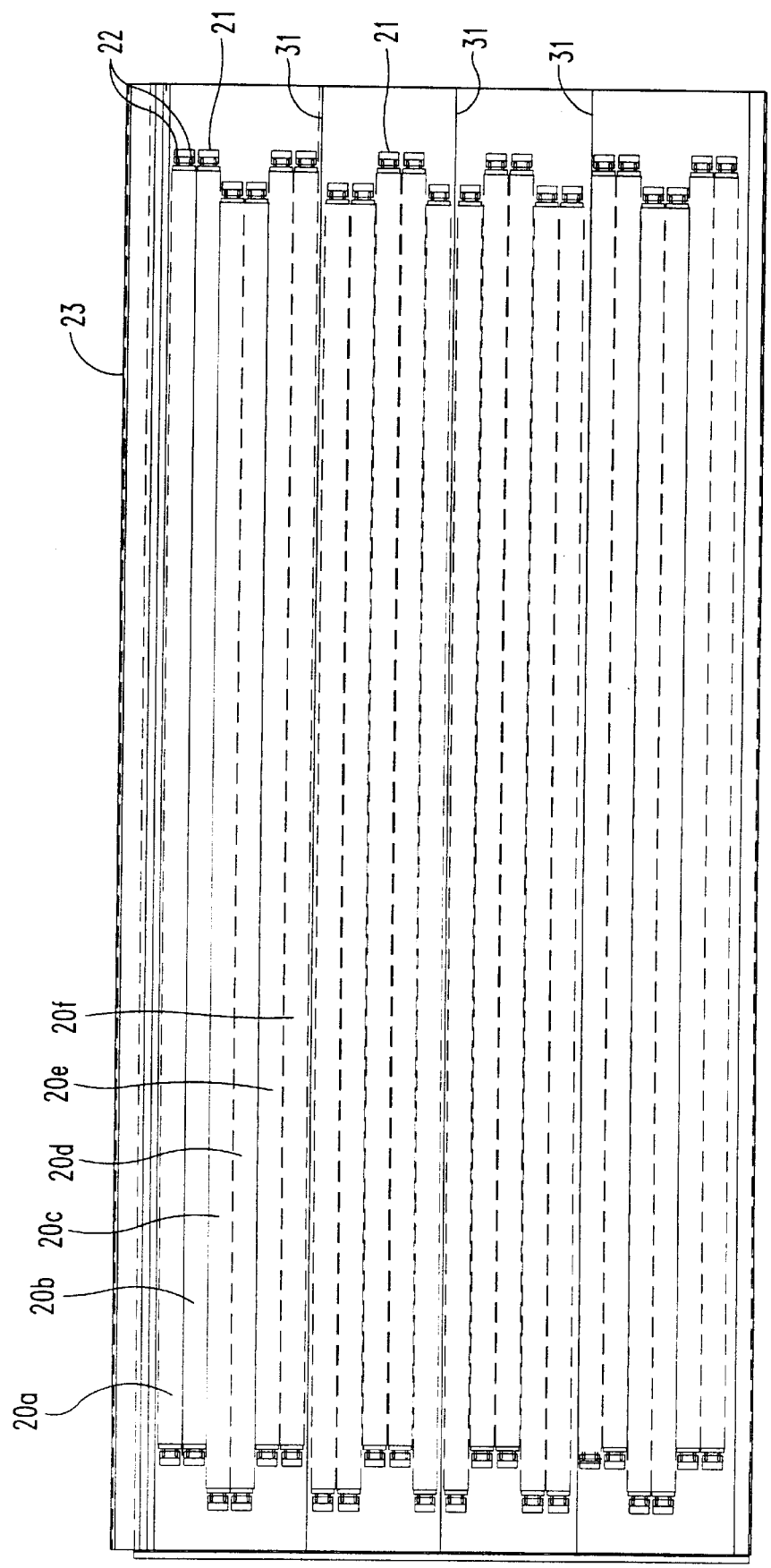
FIG. 3 is a top plan view of the lower lamp array of an alternative to FIG. 2 giving another embodiment of FIG. 1 where the lamps are offset in pairs.

FIG. 3 relates to an alternate offset configuration whereby the lamps 20 are offset in pairs. In this arrangement two lamps are aligned with each other then the next two lamps in sequence are offset in the same direction approximately one and one-quarter inches. This staggering in pairs continues throughout the array. For example, lamps 20a and 20b are aligned, lamp 20c is offset about one and one-quarter inches from lamp 20b, lamp 20d is aligned with lamp 20c, and lamps 20e and 20f are roughly aligned with lamps 20a and 20b. This arrangement also uses two electrical connectors 22 (typically, but not necessarily, pins) on each end of each lamp 20 that engage into a lamp socket 21 that is connected to the base support 11. Removal of lamps is preferably done by rotating the lamp about its longitudinal axis to change alignment of the pins from an engaged position to a position allowing exit from the socket.

Figure 4:
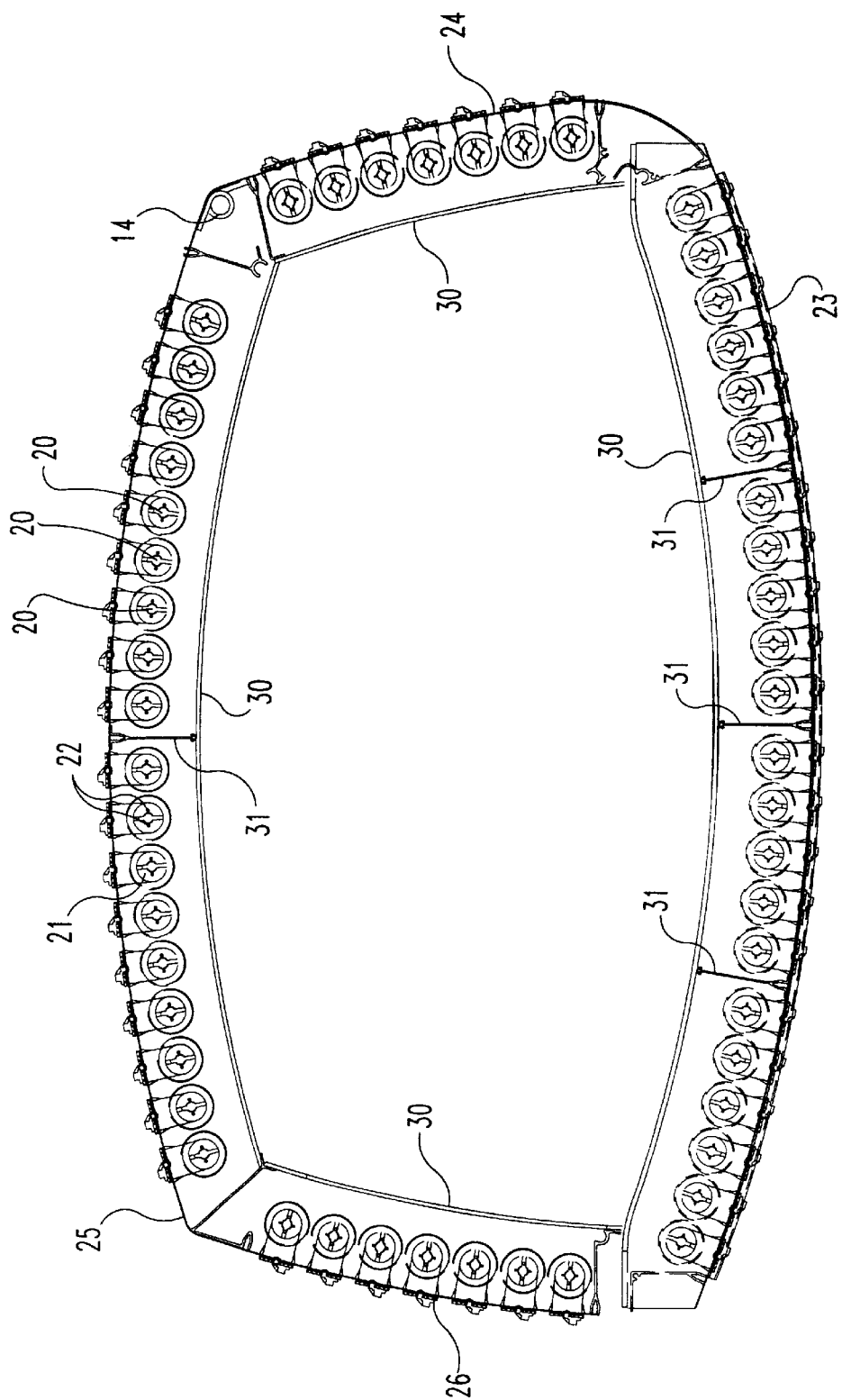
FIG. 4 is an end view of the lamp arrays in the embodiment of FIG. 1.

FIG. 4 depicts an end view of all the arrays of lamps in the tanning bed: the bottom array of lamps 23, the back-side array of lamps 24, the front-side array of lamps 26, and the top array of lamps 25. The canopy contains the front-side array of lamps 26 and the top array of lamps 25, both connected through the two electrical connectors 22 to the sockets 21 to the canopy 12. The canopy 12 is connected to the back-side array of lamps 24 by hinge 14 so that the tanning area may be opened to allow entry and exit of the tanning person. This figure also depicts the acrylic supports 31 that hold the transparent protective acrylic 30 away from the lamps 20 for physical protection of the ultraviolet lamps 20 from breakage and the tanning person from burns or over exposure, and to provide a path for cooling air near the lamps. Less preferably, a wire mesh or alternative protective structure may be substituted for the acrylic. The spacing between the lamps 20 is approximately one-sixteenth of an inch.

In one embodiment, broadly speaking the tanning bed serves as a device for illuminating a person that comprises a support member and at least three pairs of lamp sockets coupled to the support member with an array of at least three tubular fluorescent lamps, each engaged within a respective one of said pairs of lamp sockets, and in which each pair of lamp sockets is positioned so that each of the lamps has both ends longitudinally offset in the same direction from the corresponding ends of at least one tubular fluorescent lamp adjacent to it to enhance the grasping of the individual lamps.

Preferably, illuminating devices of the certain embodiments have at least seven or more, preferably sixteen, pairs of lamp sockets and fluorescent lamps. In one embodiment, every other lamp is offset longitudinally from each lamp adjacent to it while another embodiment has the lamps offset in pairs. These offsets are preferably between three-quarters of an inch and one foot. Preferably, conventional fluorescent lamp connectors having two separated conductive electrical connectors at each end are used. Of course, for the preferred tanning use of the invention, the fluorescent lamps must emit ultraviolet light suitable for tanning a person.

It is preferred that tanning devices using this invention have a distance between adjacent lamps of less than eleven-sixteenths of an inch, and more preferred that this distance is less than one-quarter of an inch, and most preferred that this distance between adjacent lamps is about one-sixteenth of an inch. Certain embodiments not shown use adjacent lamps of different diameters, but it is preferred that the lamps are of similar diameter and similar length, just longitudinally offset from one another.

While the invention is shown in the preferred context of a tanning bed, the concepts of many of the patent claims below also encompass tanning booths, tanning canopies, and other devices which emit tanning light, as well as light emitting devices without significant ultraviolet light such as may be used to lower bilirubin levels in infants, or to treat seasonal affective disorder in adults. Additionally, while the invention is shown with the lamps perfectly parallel, less preferred alternatives could be designed with each lamp being very close to an adjacent lamp at one point along their lengths, but slightly canted with respect to one another to increase the distance at other points along their lengths.

What is claimed is:

1. Body illuminating apparatus comprising:
   a support member;
   at least five pairs of lamp sockets coupled to said support member; and
   an array of at least five sequentially adjacent, substantially parallel, tubular fluorescent lamps, each engaged within a respective one of said pairs of lamp sockets, and in which each pair of lamp sockets is positioned so that each of said lamps that is sequentially adjacent to more than one tubular fluorescent lamp has both ends longitudinally offset in the same direction from the corresponding ends of at least one tubular fluorescent lamp adjacent to it to enhance the grasping of individual lamps, and in which the direction of offset changes at least once in every four adjacent lamps.

2. The apparatus of claim 1 in which the offset is three-quarters of an inch to 1 foot.

3. The apparatus of claim 1 where the fluorescent lamps have two separated conductive electrical connectors at each end.

4. The apparatus of claim 1 where the fluorescent lamps emit ultraviolet light suitable for tanning a person.

5. The apparatus of claim 1 where the distance between said adjacent lamps is about one-sixteenth of an inch.

6. The apparatus of claim 1 in which every other of said lamps is offset longitudinally from each lamp adjacent to it.

7. The apparatus of claim 6 in which the ends of every other lamp are substantially aligned.

8. The apparatus of claim 7 where the offset is about one and one-quarter of an inch.

9. The apparatus of claim 7 where the distance between said adjacent lamps is less than one-quarter of an inch.

10. The apparatus of claim 9 in which the offset is three-quarters of an inch to 1 foot for each end.

11. The apparatus of claim 7 in which the distance between said adjacent lamps is less than eleven-sixteenths of an inch.

12. The apparatus of claim 11 in which the offset is three-quarters of an inch to 1 foot for each end.

13. The apparatus of claim 12 where the fluorescent lamps have two separated conductive electrical connectors at each end.

14. The apparatus of claim 13 where the fluorescent lamps emit ultraviolet light suitable for tanning a person.

15. The apparatus of claim 1 wherein said array has at least four sequentially adjacent lamps and where the lamps are offset longitudinally in pairs.

16. The apparatus of claim 15 wherein said array has at least eight sequentially adjacent lamps and where the lamps are offset longitudinally in pairs.

17. The apparatus of claim 15 in which the distance between adjacent lamps is less than eleven-sixteenths of an inch.

18. The apparatus of claim 17 in which the offset is three-quarters of an inch to 1 foot.

19. The apparatus of claim 18 where the distance between adjacent lamps is less than one-quarter of an inch.

20. The apparatus of claim 1 in which there are at least seven pairs of lamp sockets coupled to said support member; and an array of at least seven sequentially adjacent tubular fluorescent lamps, each engaged within a respective one of said pairs of lamp sockets, and in which each pair of lamp sockets is positioned so that each of said lamps has both ends longitudinally offset in the same direction from the corresponding ends of at least one tubular fluorescent lamp adjacent to it.

21. The apparatus of claim 20 in which the offset is three-quarters of an inch to 1 foot.

22. The apparatus of claim 20 where the fluorescent lamps have two separated conductive electrical connectors at each end.

23. The apparatus of claim 20 where the fluorescent lamps emit ultraviolet light suitable for tanning a person.

24. The apparatus of claim 20 where the distance between said adjacent lamps is about one-sixteenth of an inch.

25. The apparatus of claim 20 in which every other of said lamps is offset longitudinally from each lamp adjacent to it.

26. The apparatus of claim 25 in which the ends of every other lamp are substantially aligned.

27. The apparatus of claim 26 where the offset is about one and one-quarter of an inch.

28. The apparatus of claim 26 where the distance between said adjacent lamps is less than one-quarter of an inch.

29. The apparatus of claim 28 in which the offset is three-quarters of an inch to 1 foot for each end.

30. The apparatus of claim 26 in which the distance between said adjacent lamps is less than eleven-sixteenths of an inch.

31. The apparatus of claim 30 in which the offset is three-quarters of an inch to 1 foot for each end.

32. The apparatus of claim 31 where the fluorescent lamps have two separated conductive electrical connectors at each end.

33. The apparatus of claim 32 where the fluorescent lamps emit ultraviolet light suitable for tanning a person.

34. The apparatus of claim 1 in which there are at least 16 pairs of lamp sockets coupled to said support member; and an array of at least 16 sequentially adjacent tubular fluorescent lamps, each engaged within a respective one of said pairs of lamp sockets, and in which each pair of lamp sockets is positioned so that each of said lamps has both ends longitudinally offset in the same direction from the corresponding ends of at least one lamp adjacent to it.

35. The apparatus of claim 34 in which the offset is three-quarters of an inch to 1 foot.

36. The apparatus of claim 34 where the fluorescent lamps have two separated conductive electrical connectors at each end.

37. The apparatus of claim 34 where the fluorescent lamps emit ultraviolet light suitable for tanning a person.

38. The apparatus of claim 34 where the distance between said adjacent lamps is about one-sixteenth of an inch.

39. The apparatus of claim 34 in which every other of said lamps is offset longitudinally from each lamp adjacent to it.

40. The apparatus of claim 39 in which the ends of every other lamp are substantially aligned.

41. The apparatus of claim 40 where the offset is about one and one-quarter of an inch.

42. The apparatus of claim 40 where the distance between said adjacent lamps is less than one-quarter of an inch.

43. The apparatus of claim 42 in which the offset is three-quarters of an inch to 1 foot for each end.

44. The apparatus of claim 40 in which the distance between said adjacent lamps is less than eleven-sixteenths of an inch.

45. The apparatus of claim 44 in which the offset is three-quarters of an inch to 1 foot for each end.

46. The apparatus of claim 44 where the fluorescent lamps have two separated conductive electrical connectors at each end.

47. The apparatus of claim 46 where the fluorescent lamps emit ultraviolet light suitable for tanning a person.

48. Apparatus for illuminating a portion of a human comprising:
 a support member;
 at least seven pairs of lamp sockets coupled to said support member; and an array of at least seven sequentially adjacent, substantially parallel, similar diameter tubular fluorescent lamps, each engaged within a respective one of said pairs of lamp sockets, and in which each pair of lamp sockets is positioned so that each of said lamps has both ends longitudinally offset in the same direction from the corresponding ends of at least one tubular fluorescent lamp adjacent to it, and in which the direction of longitudinal offset changes at least twice.

49. The apparatus of claim 48 in which every other of said lamps is offset longitudinally from each lamp adjacent to it.

50. The apparatus of claim 48 in which the offset is three-quarters of an inch to 1 foot.

51. The apparatus of claim 48 in which there are at least 16 pairs of lamp sockets coupled to said support member; and an array of at least 16 sequentially adjacent tubular fluorescent lamps, each engaged within a respective one of said pairs of lamp sockets, and in which each pair of lamp sockets is positioned so that each of said lamps has both ends longitudinally offset in the same direction from the corresponding ends of at least one lamp adjacent to it.

52. The apparatus of claim 48 in which the distance between adjacent lamps is less than eleven-sixteenths of an inch.

53. The apparatus of claim 52 where the distance between adjacent lamps is less than one-quarter of an inch.

54. The apparatus of claim 53 in which the distance between adjacent lamps is about one sixteenth of an inch.

* * * * *